(12) United States Patent
Ebbutt et al.

(10) Patent No.: US 11,426,237 B2
(45) Date of Patent: *Aug. 30, 2022

(54) ELECTROSURGICAL APPARATUS FOR DELIVERING RF AND/OR MICROWAVE ENERGY INTO BIOLOGICAL TISSUE

(71) Applicant: CREO MEDICAL LIMITED, Monmouthshire (GB)

(72) Inventors: Julian Mark Ebbutt, Ross-on-Wye (GB); Christopher Paul Hancock, Bath (GB); Steven Morris, Bath (GB); Malcolm White, Chepstow (GB); Brian Saunders, Rickmansworth (GB)

(73) Assignee: CREO MEDICAL LIMITED, Chepstow (GB)

( * ) Notice: Subject to any disclaimer, the term of this patent is extended or adjusted under 35 U.S.C. 154(b) by 204 days.

This patent is subject to a terminal disclaimer.

(21) Appl. No.: 16/591,118

(22) Filed: Oct. 2, 2019

(65) Prior Publication Data

US 2020/0030031 A1 Jan. 30, 2020

Related U.S. Application Data

(62) Division of application No. 15/109,077, filed as application No. PCT/GB2014/053857 on Dec. 31, 2014, now Pat. No. 10,729,495.

(30) Foreign Application Priority Data

Dec. 31, 2013 (GB) .................................. 1323171

(51) Int. Cl.
*A61B 18/18* (2006.01)
*A61B 18/14* (2006.01)
*A61B 18/00* (2006.01)

(52) U.S. Cl.
CPC .......... *A61B 18/1815* (2013.01); *A61B 18/18* (2013.01); *A61B 2018/00107* (2013.01);
(Continued)

(58) Field of Classification Search
CPC A61B 2018/00011; A61B 2018/00053; A61B 2018/00166; A61B 2018/00172;
(Continued)

(56) References Cited

U.S. PATENT DOCUMENTS 5,336,222 A 8/1994 Durgin, Jr. et al.
6,221,039 B1 * 4/2001 Durgin ............... A61B 18/1492
604/22
(Continued)

FOREIGN PATENT DOCUMENTS

CN 1283087 A 2/2001
CN 101801299 A 8/2010
(Continued)

OTHER PUBLICATIONS

Notice of Reasons for Rejection from the Japanese Patent Office in counterpart application No. 2018-239185, dated Apr. 7, 2020.
(Continued)

*Primary Examiner* — Ronald Hupczey, Jr.
*Assistant Examiner* — Bradford C. Blaise
(74) *Attorney, Agent, or Firm* — ArentFox Schiff LLP

(57) ABSTRACT

An electrosurgical instrument for applying to biological tissue RF electromagnetic energy and/or microwave frequency EM energy, wherein the instrument tip has a protective hull with a smoothly contoured convex undersurface facing away from a planar body, and wherein the planar body has a tapering distal edge, and wherein an underside of the planar body extends beyond the protective hull at the tapering distal edge. Also disclosed herein is an interface joint for integrating into a single cable assembly all of (i) a
(Continued)

fluid feed, (ii) a needle movement mechanism, and (iii) an energy feed (e.g. a coaxial cable), and a torque transfer device for permitting controlled rotation of the cable assembly within the instrument channel of an endoscope. The interface joint and torque transfer device may be integrated as a single component.

15 Claims, 9 Drawing Sheets

(52) U.S. Cl.
 CPC .............. *A61B 2018/00148* (2013.01); *A61B 2018/00166* (2013.01); *A61B 2018/00172* (2013.01); *A61B 2018/00946* (2013.01); *A61B 2018/00982* (2013.01); *A61B 2018/1405* (2013.01); *A61B 2018/1412* (2013.01); *A61B 2018/1415* (2013.01); *A61B 2018/1425* (2013.01); *A61B 2018/1861* (2013.01)

(58) Field of Classification Search
 CPC .. A61B 2018/00178; A61B 2018/0091; A61B 2018/00946; A61B 2018/00982; A61B 2018/1425; A61B 2018/1861; A61B 18/1815
 See application file for complete search history.

(56) References Cited

U.S. PATENT DOCUMENTS

| | | | | |
|---|---|---|---|---|
| 6,355,027 | B1* | 3/2002 | Le | A61M 25/0054 604/525 |
| 10,251,697 | B2 | 4/2019 | Hancock et al. | |
| 2003/0130658 | A1 | 7/2003 | Goble et al. | |
| 2006/0111710 | A1 | 5/2006 | Goble et al. | |
| 2006/0282048 | A1* | 12/2006 | Kimura | A61B 17/3478 604/272 |
| 2008/0082093 | A1 | 4/2008 | Prakash et al. | |
| 2009/0287140 | A1* | 11/2009 | Rittman, III | A61B 90/11 604/21 |
| 2010/0249769 | A1 | 9/2010 | Nau, Jr. et al. | |
| 2010/0321257 | A1* | 12/2010 | Brannan | H01Q 1/248 343/703 |
| 2011/0060326 | A1* | 3/2011 | Smith | A61B 18/18 606/33 |
| 2012/0022464 | A1* | 1/2012 | Zivkovic | A61M 5/31511 604/198 |
| 2013/0282007 | A1* | 10/2013 | Chong | A61B 5/6857 606/41 |
| 2014/0005657 | A1* | 1/2014 | Brannan | A61B 18/1815 606/33 |
| 2014/0046174 | A1* | 2/2014 | Ladtkow | A61B 10/04 600/424 |
| 2016/0120588 | A1 | 5/2016 | Amoah et al. | |
| 2016/0310701 | A1* | 10/2016 | Pai | A61M 25/0147 |
| 2020/0246068 | A1* | 8/2020 | Hancock | A61B 18/1815 |

FOREIGN PATENT DOCUMENTS

| | | |
|---|---|---|
| CN | 103329347 A | 9/2013 |
| EP | 1 905 375 A1 | 4/2008 |
| EP | 2 085 978 A2 | 8/2009 |
| EP | 2 474 283 A1 | 7/2012 |
| GB | 2 487 199 A | 7/2012 |
| GB | 2503673 A | 1/2014 |
| JP | 6-63057 A | 3/1994 |
| JP | 8-510154 A | 10/1996 |
| JP | 2000-139942 A | 5/2000 |
| JP | 2000-185053 A | 7/2000 |
| JP | 2005-512726 A | 5/2005 |
| JP | 2005-312807 A | 11/2005 |
| WO | WO 93/22977 A2 | 11/1993 |
| WO | WO 97/39707 A1 | 10/1997 |
| WO | WO 98/49933 A1 | 11/1998 |
| WO | WO 2010/053700 A1 | 5/2010 |
| WO | WO 2012/095653 A1 | 7/2012 |
| WO | WO 2013/106054 A2 | 7/2013 |

OTHER PUBLICATIONS

British Search Report of related British Patent Application No. GB1323171.7 dated Feb. 17, 2015.
Combined British Search and Examination Report of related British Patent Application No. GB1423386.0 dated Jun. 12, 2015.
Combined British Search and Examination Report of related British Patent Application No. GB1522417.3 dated Jan. 13, 2016.
International Search Report of related International Patent Application No. PCT/GB2014/053857 dated Jun. 30, 2015.
Japanese Office Action issued in corresponding Japanese Patent Application No. 2016-543172 dated Sep. 25, 2018.
Search Report, from the State Intellectual Property Office of People's Republic of China in counterpart Application No. 201480073787.2, dated Jan. 22, 2019.

* cited by examiner

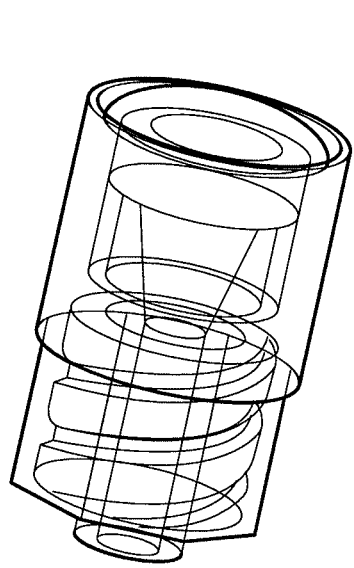
FIG. 15A
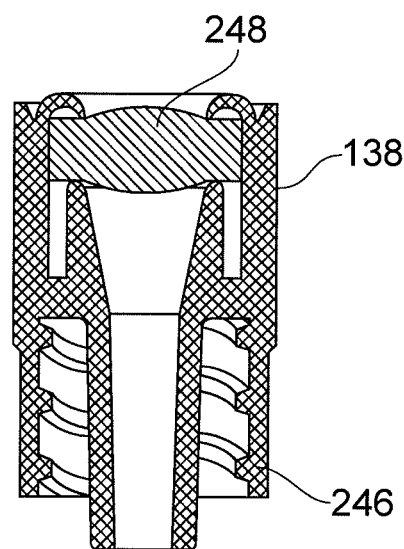
FIG. 15B
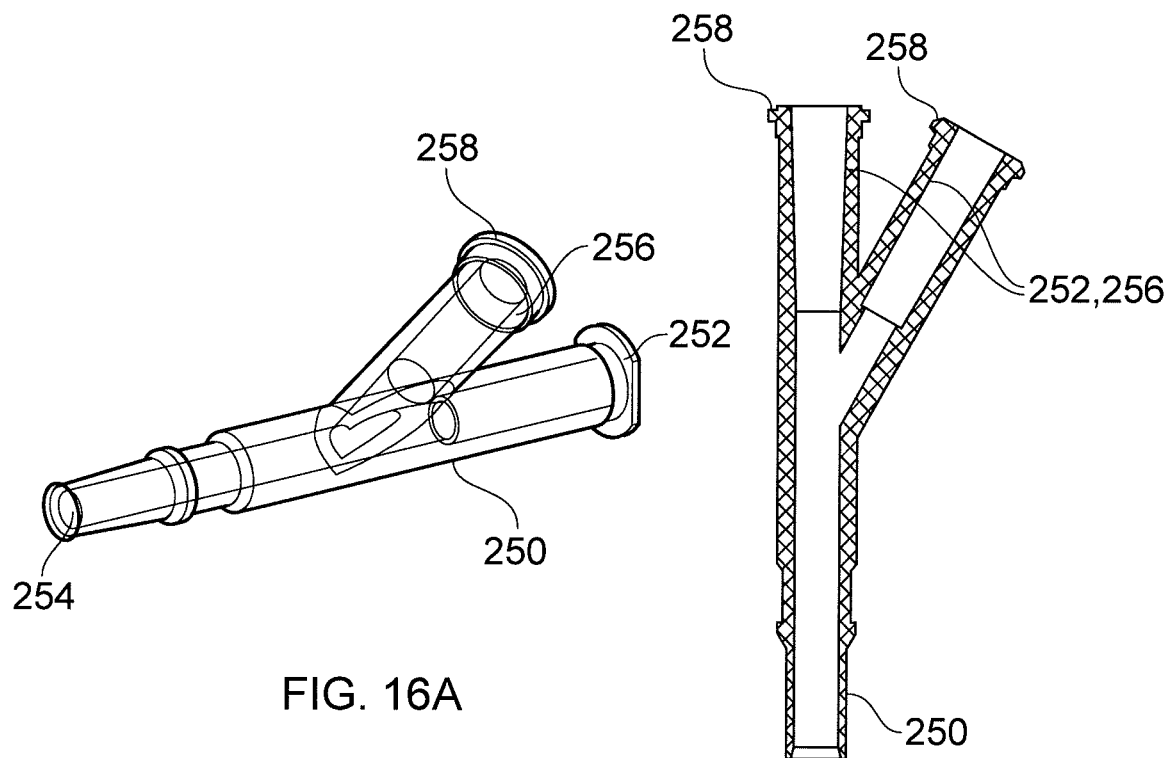
FIG. 16A
FIG. 16B

ELECTROSURGICAL APPARATUS FOR DELIVERING RF AND/OR MICROWAVE ENERGY INTO BIOLOGICAL TISSUE

CROSS-REFERENCE TO RELATED APPLICATIONS

This application is a Divisional Application of U.S. application Ser. No. 15/109,077, filed Jun. 29, 2016 (now U.S. Pat. No. 10,729,495, issued Aug. 4, 2020), which is a National Stage entry of International Application No. PCT/GB2014/053857, filed Dec. 31, 2014, which claims priority to British Patent Application No. 1323171.7, filed Dec. 31, 2013. The disclosures of the priority applications are hereby incorporated in their entirety by reference.

TECHNICAL FIELD

The invention relates to an electrosurgical apparatus and device for delivering radiofrequency and/or microwave frequency energy into biological tissue. In particular, the invention relates to an electrosurgical instrument capable of delivering radiofrequency (RF) energy for cutting tissue and/or microwave frequency energy for haemostasis (i.e. promoting blood coagulation). The invention may be particularly suitable for use in gastrointestinal (GI) procedures associated with the lower and upper GI tract, e.g. to remove polyps on the bowel, i.e. for endoscopic mucosal resection, or endoscopic submucosal dissection. The invention may also lend itself to other procedure, e.g. in general surgery or laparoscopic surgery. The invention may find use in ear, nose and throat procedures and liver resection. The device may also be used to address procedures associated with the pancreas, e.g. to resect or remove tumours or abnormalities in close proximity to the portal vein or the pancreatic duct.

BACKGROUND TO THE INVENTION

Surgical resection is a means of removing sections of organs from within the human or animal body. Such organs may be highly vascular. When tissue is cut (divided or transected) small blood vessels called arterioles are damaged or ruptured. Initial bleeding is followed by a coagulation cascade where the blood is turned into a clot in an attempt to plug the bleeding point. During an operation, it is desirable for a patient to lose as little blood as possible, so various devices have been developed in an attempt to provide blood free cutting. For endoscopic procedures, bleeds are also undesirable, and need to be dealt with in an expedient manner, since the blood flow may obscure the operator's vision, which may prolong surgery and potentially lead to the procedure needing to be terminated and another method used instead, e.g. open surgery.

Electrosurgical generators are prevalent in hospital operating theatres, often for use in open and laparoscopic procedures, and increasingly for use in endoscopy suites. In endoscopic procedures the electrosurgical accessory is typically inserted through a lumen inside an endoscope. Considered against the equivalent access channel for laparoscopic surgery, such a lumen is comparatively narrow in bore and greater in length.

Instead of a sharp blade, it is known to use radiofrequency (RF) energy to cut biological tissue. The method of cutting using RF energy operates using the principle that as an electric current passes through a tissue matrix (aided by the ionic contents of the cells and the intercellular electrolytes), the impedance to the flow of electrons across the tissue generates heat. In practice, an instrument is arranged to apply an RF voltage across the tissue matrix that is sufficient to generate heat within the cells to vaporise the water content of the tissue. However, as a result of this increasing desiccation, particularly adjacent to the RF emitting region of the instrument (which has the highest current density of the current path through tissue), direct physical contact between the tissue and instrument can be lost. The applied voltage then manifests itself as a voltage drop across this small void, which causes ionisation in the void that leads to a plasma. Plasma has a very high volume resistivity compared with tissue. The energy supplied to the instrument maintains the plasma, i.e. completes the electrical circuit between the instrument and the tissue. Volatile material entering the plasma can be vaporised and the perception is therefore of a tissue dissecting plasma.

GB 2 472 972 describes an electrosurgical instrument in the form of a spatula comprising a planar transmission line formed from a sheet of a first dielectric material having first and second conductive layers on opposite surfaces thereof, the planar transmission line being connected to a coaxial cable that is arranged to deliver either microwave or RF energy to the planar transmission line, the coaxial cable comprising an inner conductor, an outer conductor coaxial with the inner conductor, and a second dielectric material separating the outer and inner conductors, the inner and outer conductors extending beyond the second dielectric at a connection interface to overlap opposite surfaces of the transmission line and electrically contact the first conductive layer and second conductive layer respectively. The first conductive layer is spaced from the end of the transmission line that abuts the coaxial cable to electrically isolate the outer conductor from the first conductive layer and also the distance of the gap is involved with matching the impedance of the energy delivered from the microwave source with the impedance of the biological tissue, and the width of the first and second conductive layers is also selected to help create an impedance match between the transmission line and the coaxial cable.

The spatula configuration set forth in GB 2 472 972 provides desirable insertion loss between the co-axial feed line and the end radiating section, whilst also providing desirable return loss properties for the edges of the spatula when in contact with air and biological tissue respectively. In more detail, the insertion loss along the structure may be less than 0.2 dB at the frequency of interest, and the return loss less than (more negative than) −1 dB, preferably less than −10 dB. These properties may also indicate a well matched junction between the coaxial cable and the transmission line spatula structure, whereby microwave power is launched efficiently into the spatula. Similarly, when the edges of the spatula are exposed to air or biological tissue that is not of interest, the return loss may be substantially zero (i.e. very little power radiated into free space or undesirable tissue), whereas when in contact with desirable biological tissue the return loss may be less than (more negative than) −3 dB, preferably less than −10 dB (i.e. the majority of power in the spatula is transferred to the tissue).

The instrument discussed in GB 2 472 972 is intended to radiate microwave energy from the edges of the planar transmission line to cause localised tissue ablation or coagulation.

GB 2 472 972 also discloses that the spatula discussed above may have an RF cutting portion integrated therewith. The RF cutting portion may be formed by using the first and second conductive layers mentioned above as active and return electrodes for RF energy. This arrangement may take advantage of the fact that the active and return electrodes are in close proximity to one another, thus setting up a preferential return path to enable local tissue cutting action to take place without the need for a remote return pad or a highly conductive liquid, i.e. saline, existing between the two electrodes.

In this example, the RF cutting portion may comprise a RF voltage source coupled to the planar transmission line, a frequency diplexer/duplexer unit (or signal adder) comprising a low pass filter to prevent the high frequency microwave energy from going back into the lower frequency RF energy source and a high pass filter to prevent the lower frequency RF energy from going back into the higher frequency microwave energy source. In one example, the frequency diplexer/duplexer may be used to enable the microwave and RF energy sources to be combined at the generator and delivered along a single channel, e.g. co-axial cable, waveguide assembly or twisted pair, to the spatula structure. The RF cutting energy may be delivered alone into the tissue or it may be mixed or added with the microwave energy and delivered simultaneously to set up a blended mode of operation.

SUMMARY OF THE INVENTION

The present invention develops further the spatula concept discussed in GB 2 472 972 and the manner with which it interfaces with a generator that provides RF and/or microwave energy for treatment.

In a first aspect, the invention provides an further optimised configuration for the distal end of an electrosurgical tool for controlled resection of biological tissue.

In a second aspect, the invention provides an interface joint for integrating into a single cable assembly all of (i) a fluid feed, (ii) a needle movement mechanism, and (iii) an energy feed (e.g. a cable supplying RF and/or microwave energy). The cable assembly may be sized to fit through the instrument channel of a conventional endoscope.

In a third aspect, the invention provides a torque transfer device for permitting controlled rotation of the cable assembly within the instrument channel of the endoscope. The interface joint and torque transfer device may be integrated as a single component.

According to the first aspect of the invention, there is provided an electrosurgical instrument for applying to biological tissue radiofrequency (RF) electromagnetic (EM) energy and/or microwave frequency EM energy, the instrument comprising: an instrument tip comprising a planar body made of a first dielectric material separating a first conductive element on a first surface thereof from a second conductive element on a second surface thereof, the second surface facing in the opposite direction to the first surface; a coaxial feed cable comprising an inner conductor, an outer conductor coaxial with the inner conductor and a second dielectric material separating the inner and outer conductors, the coaxial feed cable being for conveying an RF signal and/or a microwave signal; and a protective hull comprising a third piece of dielectric material mounted to cover the underside of the planar body, wherein the inner conductor is electrically connected to the first conductive element and the outer conductor is electrically connected to the second conductive element to enable the instrument tip to receive the RF signal and/or the microwave signal, wherein the protective hull has a smoothly contoured convex undersurface facing away from the planar body, wherein the planar body has a tapering distal edge, and wherein the underside of the planar body extends beyond the protective hull at the tapering distal edge. This combination of features represents an optimal configuration that balances the accuracy of treatment at the distal tip (which is enhanced due to the extension of the planar body over the protective hull) with the ease of safe manipulation of the instrument (due to the protective hull itself).

The portion of the underside of the planar body that extends beyond the protective hull at the tapering distal edge may be termed the extension zone. The extension zone may be uniform around the perimeter of the tapering distal edge. Alternatively, the extension zone itself may taper in width towards the distal tip of the planar body. The tapering may be between a minimum value at the distal tip and a maximum value at the proximal end of the tapering distal edge. There may be zero extension at the distal tip, i.e. the protective hull may be contiguous (i.e. flush) with the planar body at that point. The extension zone may be sized to provide a beneficial impact on the energy fields emitted by the device, but without adversely impacting the function of the protective hull.

The magnitude of the extension zone may be related to, e.g. in proportion to, the geometry of the distal tip. The planar body may have any dimensions suitable for use in a particular procedure. For example, for endoscopic procedures, the instrument may have an overall outer diameter of 2.3 mm or less, preferably 1.2 mm or less. The width of the planar body may thus be 2 mm of less. However, other procedures may be less restrictive, whereby the width of the planar body may be up to 9 mm. The width of the extension zone, i.e. the distance by with the tapering distal edge extends beyond the protective hull in a direction normal to the edge of the protective hull may be 0.2w or less, preferably 0.1w or less, where w is the maximum width of the planar body (i.e. the maximum dimension of the planar body in the direction of the diameter of the lumen or catheter through which it is inserted in use. Thus, for a planar body having a width of 2 mm, the extension zone may have a maximum width of 0.2 mm.

In use, the first and second conductive elements may be arranged to provide a local return path for RF energy, i.e. a low impedance route for RF energy to be transported between the first and second conductive elements. The first and second conductive elements may be layers of metallisation formed on opposite surfaces of the first dielectric material. The first and second conductive elements may be arranged to set up a local electric field at a contact region in which the instrument tip makes contact with the biological tissue. The local electric field can be extremely high, which may cause a microplasma (i.e. a hot thermal plasma) to be formed at the distal side portion of the planar body, e.g. where contact is made with the biological tissue. The microplasma may be desirable in terms of achieving efficient cutting.

Meanwhile, for a microwave signal, the instrument tip may be modelled as a parallel plate transmission line with the planar body representing dielectric material separating two conductive plates. The radiation pattern of the microwave frequency EM energy in this case depends on the overall shape of the planar body and the microwave feed structure. In this particular instance, the gap at the proximal end between the co-axial feed line (centre conductor) and the upper conductive layer plays an important role in ensuring that the microwave energy from the source is matched in terms of impedance with the load impedance presented by the tissue. The overall length of the planar transmission line arrangement is also important in terms of matching the impedance (or the energy delivery) of (or from) the coaxial transmission line with (or into) the biological tissue, i.e. the structure may form a quarter wave impedance transformer or a half wavelength resonator. Using known simulation tools, this may be modelled to control from which edges the microwave frequency EM energy is radiated. For example, the instrument tip may be configured to inhibit radiation of the microwave EM radiation from a distal edge of the planar body.

The tapering distal edge may have any suitable profile, e.g. obtained by computer modelling the device in particular use configurations. The tapering distal edge may be curved or straight or a combination of the two. For example, the tapering distal edge may comprise a straight taper terminated in a curved distal tip, e.g. a single radius curved distal tip. The tapering distal edge may extends around a distal third of planar body. In one embodiment, the curved distal edge may have a curvature formed from a plurality of contiguous radiused sections, each radiused section having a radius of curvature less than its proximal neighbour. There may be three of more section of different radii. The plurality of contiguous radiused sections may be arranged to give the curved distal edge a quasi parabolic shape.

As mentioned above, the width of the planar body may be dictated by the intended use for the instrument. In endoscopic procedures, the width may be 2 mm or less, whereas for other less restrictive procedures the width may be up to 9 mm, e.g. any of 8 mm or less, 7 mm or less, 6 mm or less, 5 mm or less, 4 mm or less or 3 mm or less.

The length of the planar body (including the tapering distal end) may be related to, e.g. in proportion with, its width in order to deliver the RF and/or microwave frequency energy most efficiently. The length of the planar body may thus be about 5w, e.g. between 5w and 6w, preferably 5.3w where w is the maximum width of the planar body.

In one embodiment, the planar body has a maximum width of 2 mm and a maximum length of 10.6 mm. In this embodiment, the tapering distal edge may comprise a plurality of contiguous radiused sections consisting of a first radiused section having a length of 1.6 mm and a radius of curvature of 12.4 mm, a second radiused section having a length of 1.0 mm and a radius of curvature of 10.2 mm, a third radiused section having a length of 0.7 mm and a radius of curvature of 3.2 mm, a fourth radiused section having a length of 0.2 mm and a radius of curvature of 0.85 mm, and a fifth radiused section having a length of 0.1 mm and a radius of curvature of 0.35 mm.

The first and second conductive elements may each comprise a layer of metallisation, the layers of metallisation being formed on opposite surfaces of the first dielectric material. The layers of metallisation may be set back (e.g. by 0.2 mm) from the side edges of the first dielectric material in a proximal region of the planar body, to reduce the field strength at this region. The proximal region may comprise the region of the planar body proximal to the curved distal end. This may help concentrate the energy delivery at the distal end. The inner conductor and outer conductor may contact the first and second conductive elements in a coaxial manner, i.e. the first and second conductive elements may be shaped to be symmetric about an axis running along the planar body from the coaxial feed cable.

The undersurface of the protective hull may smoothly taper at its perimeter to meet the underside of the planar body. The thickness of the protective hull may also decrease towards the distal end of the instrument tip. Thus, the outer portion of the protective hull may have a convex profile. The undersurface may have a longitudinally extending recessed channel formed therein. The tapering edge profile and recessed channel may cause the undersurface of the protective hull to comprise a pair of ridges. The tapered conformal flowing form of the hull may reduce the risk of the instrument digging into collateral tissue aiding its ability to glide. For example, this shape may reduce the risk of the instrument digging into the bowel wall and causing a bowel perforation or may protect the portal vein or pancreatic duct from being damaged. The particular dimensions of the hull (e.g. length, width, thickness, etc.) may be adapted to suit the intended use and intended area of the body to be operated on.

The protective hull may be formed from a biocompatible non-conductive material, such as polyether ether ketone (PEEK), ceramic (e.g. alumina, zirconia or zirconia toughened alumina (ZTA)) or biocompatible plastic that does not stick to the wall of the bowel (or other biological tissue) or the like. Alternatively, the hull may also be formed from a metallic material, e.g. titanium, steel, or may be a multilayer structure. It may be attached (e.g. bonded) to whichever one of the first or second conductive elements is on the underside of the first dielectric material. However, in one embodiment, the protective hull may be formed of the same material as the first dielectric material. The protective hull and first dielectric material may be formed in one piece as a unitary body. In this arrangement one or more planar slots may be formed (e.g. cut) in the unitary body to allow a conductive material to be inserted to form the first and/or second conductive material. The conductive material may be inserted by coating one or more internal surfaces of the slot. Alternatively or additionally, the protective hull may be selectively metallised to form part of the first or second conductive elements.

The instrument may include a fluid feed conduit for delivering fluid (e.g. saline) to the instrument tip. The fluid feed conduit may comprise a passageway through the protective hull for delivering fluid to the treatment site. The passageway may include an outlet located in the recessed channel of the protective hull. The coaxial feed cable may form part of a multi-lumen conduit assembly for delivering RF and/or microwave frequency energy and fluid (liquid or gas) to the instrument. The fluid (protective hull) may be conveyed through a corresponding passageway formed within the multi-lumen conduit assembly. The fluid feed conduit may also be used to deliver other material to the treatment site, e.g. a gas or a solid (e.g. powder). In one embodiment, injection of fluid (saline or the like) is used to plump up the biological tissue at the treatment site. This may be particularly useful where the instrument is used to treat the wall of the bowel or the wall of the esophagus or for protecting the portal vein or the pancreatic duct when a tumour or other abnormality located in close proximity, in order to protect these structures and create a cushion of fluid. Plumping up the tissue in this manner may help to reduce the risk of bowel perforation, damage to the wall of the esophagus or leakage of from the pancreatic duct or damage to the portal vein, etc. This aspect of the invention may make it capable of treating other conditions where the abnormality (tumour, growth, lump, etc.) is close to a sensitive biological structure.

It is advantageous to be able to use the same instrument to deliver fluid as delivers RF and/or microwave energy since deflation (e.g. due to fluid seepage or loss of insufflation air) may occur if a separate instrument is introduced into the region or during treatment. The ability to introduce fluid using the same treatment structure enables the level to be topped up as soon as deflation occurs. Moreover, the use of a single instrument to perform desiccation or dissection as well as to introduce fluid also reduces the time taken to perform the overall procedure, reduces the risk of causing harm to the patient and also reduces the risk of infection. More generally, injection of fluid may be used to flush the treatment region, e.g. to remove waste products or removed tissue to provide better visibility when treating. As mentioned above, this may be particularly useful in endoscopic procedures.

The undersurface of the protective hull may have a longitudinally extending recessed channel formed therein, and the fluid delivery mechanism may include an insulating needle guide tube mounted within and extends proximally from the recess channel, and a retractable needle (e.g. hypodermic needle) slidably mounted in the needle guide tube. The needle may have an outer diameter less than 0.6 mm, e.g. 0.4 mm. The needle may be movable in the longitudinal direction between a deployed position in which it protrudes beyond the distal end of the instrument tip and a retracted position in which it is set back from the distal edge of the instrument tip, e.g. below the planar body or locates proximal to the planar body.

Alternatively, the fluid feed conduit may comprise a tubular (e.g. conical) protrusion integrally formed in the protective hull, e.g. on an undersurface thereof. The tip of the protrusion may have an outlet for a fluid passage, and thus may act as a fixed needle-like tip for fluid injection into the tissue. The tip of the cone may project slightly beyond the distal tip of the planer body.

According to the second aspect of the invention, there is provided an interface joint for interconnecting an electrosurgical generator and an electrosurgical instrument (which may be an instrument according to the first aspect of the invention), the interface joint comprising: a housing made of electrically insulating material, the housing having: a first inlet for receiving radiofrequency (RF) electromagnetic (EM) energy and/or microwave frequency EM energy from the electrosurgical generator, a second inlet for receiving fluid, and an outlet; a single cable assembly for connecting the outlet to the electrosurgical instrument, the signal cable assembly comprising a flexible sleeve that defines a fluid flow path that is in fluid communication with the second inlet, and which conveys a coaxial cable that is connected to the first inlet.

The electrosurgical generator may be any device capable of delivery RF EM energy or microwave frequency EM energy for treatment of biological tissue. For example, the generator described in WO 2012/076844 may be used.

The electrosurgical instrument may be any device which in use is arranged to use RF EM energy or microwave frequency EM energy for the treatment of biological tissue. The electrosurgical instrument may use the RF EM energy and/or microwave frequency EM energy for any or all of resection, coagulation and ablation. For example, the instrument may be a resection device as disclosed herein, but alternatively may be any of a pair of microwave forceps, a snare that radiates microwave energy and/or couples RF energy, and an argon beam coagulator.

The housing may provide a double isolation barrier for the operator, i.e. the housing may comprise an outer casing (first level of isolation) that encapsulates a branched passageway (second level of isolation) within which the various inputs are integrated into the single cable assembly. The branched passageway may provide a watertight volume which defines a fluid flow path between the second inlet and the outlet, and which has a first port adjacent to the first inlet for admitting the coaxial cable.

In use, the interface joint may be the location at which fluid for treatment at the instrument is introduced. The operator of the interface joint may control the introduction of fluid, e.g. via a syringe or other fluid introducing mechanism attached to the second inlet. The interface joint may also include a fluid delivery deployment mechanism that acts to instruct or control fluid delivery at the electrosurgical instrument. For example, the interface joint may include a slidable trigger on the housing, the slidable trigger being attached to a push rod that extends out of the housing through the outlet. The push rod may extend through the flexible shaft to the electrosurgical instrument, where it can control the fluid delivery structure. For example, the electrosurgical instrument may include a retractable needle that is switchable into and out of fluid communication with the fluid flow path in the flexible shaft by sliding the push rod back and forth.

In this arrangement, the branched passageway may include a second port adjacent the slidable trigger for admitting the push rod.

Both the first port and the second port may comprise a sealing bung which defines a watertight passage for the coaxial cable and the push rod respectively. The sealing bung may be formed from a resiliently deformable material, e.g. silicone rubber, whereby the coaxial cable and push rod are encapsulated in the material as they pass through it. Sealing the first and second ports in this way means that the only route for fluid out of the interface joint is through the outlet along the fluid flow path in the flexible sleeve.

The branched passageway may have any suitable configuration. In one embodiment, it is formed from a pair of Y-shaped conduits, which are connected to each over to define a first length in line with the outlet, a second length extending from a side of the first length at an oblique angle to the first length, and a third length extending from a side of the second length. The first length may have the push rod extending through it and may terminate at is proximal end in a sealing bung. The second length may have the coaxial cable running through it and may terminate at its proximal end in a sealing bung. The third length may terminate in the second port for receiving the fluid. In this arrangement, the housing may have a pistol-like shape. However, in another embodiment, the branched passageway may have a more compact configuration, in which the different lengths of the passageway run substantially parallel to each other. In this arrangement, the housing may be an elongate capsule sized to fit in an operator's hand.

The interface joint may be particular suitable for gathering a plurality of inputs into a single cable assembly (i.e. the multi-lumen cable assembly mentioned above) before it is inserted through the instrument channel of an endoscope. To achieve this, the cable assembly may have an outer diameter of 9 mm or less, e.g. 2.8 mm or less for a flexible video colonoscope.

In order to facilitate manipulation of the instrument at the distal end of the instrument channel of the endoscope, the flexible sleeve may be provided with longitudinal braids therein to assist in the transfer of torque, i.e. to transfer a twisting motion at the proximal end of the cable assembly to the distal end of the cable assembly, where it can cause bi-rotational rotation of the instrument because the instrument is attached to the cable assembly. The flexible sleeve may comprises a inner tube and an outer tube, which are bonded or otherwise attached together with a tube of metallised braiding in between. The pitch of the braiding may be variable along the length of the cable assembly. For example, it may be useful to have a wider pitch in a region e.g. a distal portion of the cable, where flexibility is important. In order to prevent the metallised braiding from interfering with the RF field or microwave field at the instrument, a distal portion of the flexible sleeve may be provided in which the braided is absent. The distal portion may be manufactured separately and attached (e.g. bonded or welded) to the braided portion.

The housing may further comprise a strain relief element mounted in the outlet and surrounding the flexible sleeve. The function of the strain relief element is to limit the movement of the sleeve in this location to prevent overflexing that may damage the internal components.

The flexible sleeve may comprise a multi lumen tube. The lumens may be formed by inserting an extruded separator element inside a single lumen tube. The extruded separator element may include a plurality of through channels (e.g. two, three or more). One of the through channels may carry the push rod (if present). The other channels may be left empty, which can ensure that there is always a open fluid flow path between the instrument and interface joint for guiding the coaxial cable and one or more through holes for carrying the fluid feed conduit and control wire(s). The fluid flow path may flood the internal cavity formed by the flexible sleeve, and the coaxial cable may be immersed in the fluid.

A distal end of the push rod may be connected to a proximal end of a needle ferrule, which has a needle clamped to its distal end. The ferrule may be hollow, with one or more openings in its outer wall that cause its interior to be in fluid communication with the fluid flow path through the flexible sleeve. The distal end of the ferrule may be open such that the needle mounted in the distal end is in fluid communication with the fluid flow path. The proximal end of the ferrule may be sealed by the push rod.

According to the third aspect of the invention, there is provided a torque transfer unit for rotating an electrosurgical instrument at the distal end of an endoscope by transferring a user's rotating force to a flexible sleeve connected to the electrosurgical instrument, wherein the torque transfer unit comprises an elongate clamp arranged to impart a gripping force along a length of the flexible sleeve that lies outside the endoscope, the elongate clamp comprising: an upper elongate housing member, a lower elongate housing member pivotably connected to the upper elongate housing member and defining a passage for the flexible sleeve, wherein the upper elongate housing member and the lower elongate housing member are pivotable between a release position in which the torque transfer unit is slidable up and down the flexible sleeve, and a clamping position, in which the flexible sleeve is gripped between the upper elongate housing member and the lower elongate housing member.

The torque transfer unit may thus be designed to slide freely along the length of the flexible sleeve to a position that is convenient for use. Once in position, the torque transfer unit can grip the sleeve by pivoting the upper elongate housing member and the lower elongate housing member together. The torque transfer unit may include a releasable clip that allows the upper elongate housing member and the lower elongate housing member to be locked in place at any point. The clip may be a resilient latch element on one of the upper elongate housing member and the lower elongate housing member, which a corresponding catch on the other.

The upper elongate housing member and the lower elongate housing member may each carry a U-shaped clamping member, the U-shaped clamping members being arranged to oppose one another to impart a substantially uniform gripping pressure on the flexible sleeve when the upper elongate housing member and the lower elongate housing member are in the clamping position. In a preferred embodiment, an intermediate deformable grip tube is position around the flexible sleeve between the flexible sleeve and the U-shaped clamping members. The intermediate grip tube may be made of silicone or any other suitable compliant material. In use the intermediate deformable grip tube grips the flexible sleeve on compression and fixes the position of the torque transfer unit. The intermediate grip tube acts to distribute the load on the flexible sleeve which can prevent local damage to the wall of the sleeve.

In use, when the distal tip of the electrosurgical instrument is correctly positioned relative to the distal end of the flexible endoscope within the field of view on the endoscope's video monitor, it is intended that the endoscopist clamps and locks the torque transfer unit at the exit point of the flexible shaft from the endoscope working channel and immediately adjacent to the endoscope X-Y controls. When clamped in this location the torque transfer unit provides finger and thumb rotary and longitudinal positional control of the distal tip of the instrument. The variable positioning and clamping of the torque transfer unit allows the instrument to be used endoscopes of differing lengths (e.g. flexible endoscopes with working channels anywhere between 60 and 170 cm long).

Herein, radiofrequency (RF) may mean a stable fixed frequency in the range 10 kHz to 300 MHz and microwave frequency may mean a stable fixed frequency in the range 300 MHz to 100 GHz. The RF energy should have a frequency high enough to prevent the energy from causing nerve stimulation and low enough to prevent the energy from causing tissue blanching or unnecessary thermal margin or damage to the tissue structure. Preferred spot frequencies for the RF energy include any one or more of: 100 kHz, 250 kHz, 400 kHz, 500 kHz, 1 MHz, 5 MHz. Preferred spot frequencies for the microwave energy include 915 MHz, 2.45 GHz, 5.8 GHz, 14.5 GHz, 24 GHz.

BRIEF DESCRIPTION OF THE DRAWINGS

Examples embodying the invention as discussed in detail below with reference to the accompanying drawings, in which:

FIG. 15A is a perspective view of a stopper used in the interface joint shown in FIG. 2;

FIG. 15B is a cross-sectional view through the stopper shown in FIG. 15A;

FIG. 16A is a perspective view of a Y-shaped connector used in the interface joint shown in FIG. 2;

FIG. 16B is a cross-sectional view through the Y-shaped connector shown in FIG. 16A;

DETAILED DESCRIPTION; FURTHER OPTIONS AND PREFERENCES

Various aspects of the present inventions are presented below in the context of an electrosurgery system that provides an electrosurgical invasive instrument for use in endoscopic procedures for the removal of polyps and malignant growths through the controlled delivery of both microwave and RF energy. However, it is to be understood that the aspects of the invention presented herein need not be limited to this particular application. They may be equally applicable in embodiments where only RF energy is required, or where only RF energy and fluid delivery is required.

Figure 1:
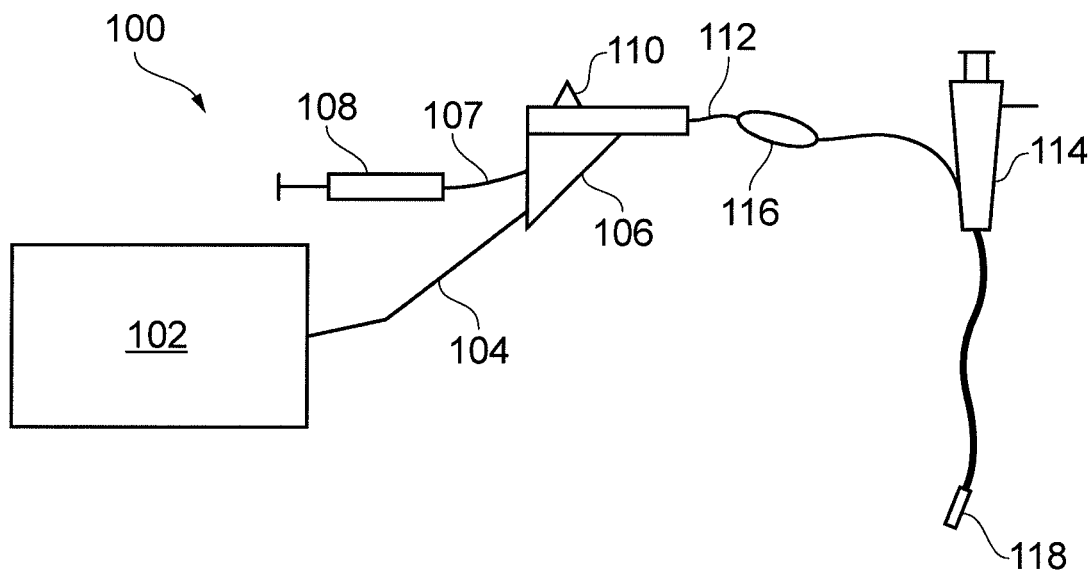
FIG. 1 is a schematic view of a complete electrosurgery system in which the present invention is applied.

FIG. 1 is a schematic diagram of a complete electrosurgery system 100 that is capable of selectively supplying to the distal end of an invasive electrosurgical instrument any or all of RF energy, microwave energy and fluid, e.g. saline or hyaluronic acid. The system 100 comprises a generator 102 for controllable supplying RF electromagnetic (EM) energy and/or microwave frequency EM energy. A suitable generator for this purpose is described in WO 2012/076844, which is incorporated herein by reference.

The generator 102 is connected to an interface joint 106 by an interface cable 104. The interface joint 106 is also connected to receive a fluid supply 107 from a fluid delivery device 108, such as a syringe. The interface joint 106 houses a needle movement mechanism that is operable by sliding a trigger 110. The function of the interface joint 106 is to combine the inputs from the generator 102, fluid delivery device 108 and needle movement mechanism into a single flexible shaft 112, which extends from the distal end of the interface joint 106. The internal configuration of the interface joint 106 is discussed in more detail below.

The flexible shaft 112 is insertable through the entire length of an instrument (working) channel of an endoscope 114. A torque transfer unit 116 is mounted on a proximal length of the shaft 112 between the interface joint 106 and endoscope 114. The torque transfer unit 116 engages the shaft to permit it to be rotated within the instrument channel of the endoscope 114.

The flexible shaft 112 has a distal assembly 118 that is shaped to pass through the instrument channel of the endoscope 114 and protrude (e.g. inside the patient) at the distal end of the endoscope's tube. The distal end assembly includes an active tip for delivering RF EM energy and/or microwave EM energy into biological tissue and a retractable hypodermic needle for delivering fluid. These combined technologies provide a unique solution for cutting and destroying unwanted tissue and the ability to seal blood vessels around the targeted area. Through use of the retractable hypodermic needle, the surgeon is able to inject saline and/or hyaluronic acid with added marker dye between tissues layers in order to distend and mark the position of a lesion to be treated. The injection of fluid in this manner lifts and separates the tissue layers making it both easier to resect around the lesion and plane through the submucosal layer, reducing the risk of bowel wall perforation and unnecessary thermal damage to the muscle layer.

As discussed in more detail below, the distal assembly 118 further includes a protective polymer hull positioned under the active tip to assist a tissue planing type resection action, again helping to protect against inadvertent perforation and ensure viability of the remaining tissue, which in turn facilitates more rapid healing and post operation recovery.

The structure of the distal assembly discussed below may be particularly designed for use with a conventional steerable flexible endoscope having a working channel with an internal diameters of at least 2.8 mm and a channel length of between 60 cm and 170 cm. As such the majority of the comparatively small diameter (less than 3 mm) instrument is housed within the lumen of a much larger and predominantly polymer insulating device, i.e. the flexible endoscope channel, which typically has an outer diameter of 11 mm to 13 mm. In practice, only 15 mm to 25 mm of the distal assembly protrudes from the distal end of the endoscope channel, in order not to block the field of view or adversely affect camera focussing. The protruding part of the distal assembly is the only portion of the instrument that ever makes direct contact with the patient.

At the proximal end of the endoscope working channel, which is typically held 50 cm to 80 cm from the patient, the flexible shaft 112 emerges from the working channel port and extends a further 30 cm to 100 cm to the interface joint 106. In use, the interface joint 106 is typically held by a gloved assistant throughout the procedure. The interface joint 106 is designed and manufactured from polymer materials in such a way as to provide primary and secondary electrical insulation with extended creepage and clearance distances. The interface cable 104 is connected to the generator 102 using a QMA-type coaxial interface, which is designed to allow continuous clockwise or counter clockwise rotation. This permits the interface joint 106 to rotate with the torque transfer unit 116 under the control of the endoscopist. The assistant supports the interface joint 106 throughout the procedure in order to assist the endoscopist with sympathetic instrument rotation, needle control and fluid injection.

Interface Joint & Torque Transfer Unit

Figure 2:
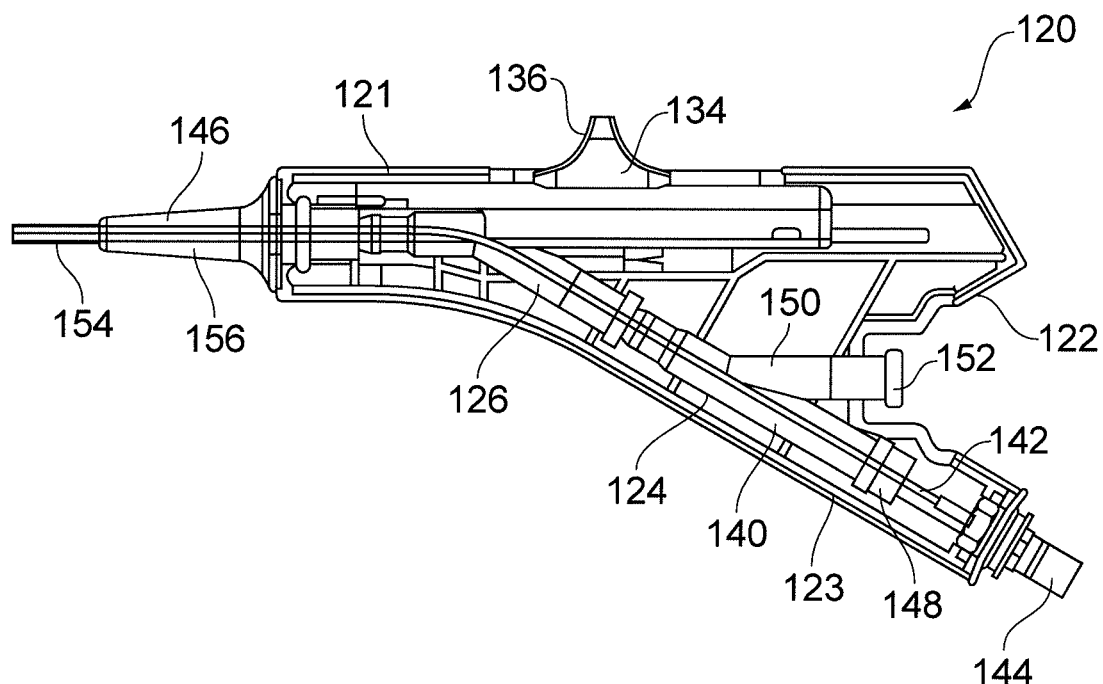
FIG. 2 is a cross-sectional view of an interface joint that is an embodiment of the invention.
Figure 3:
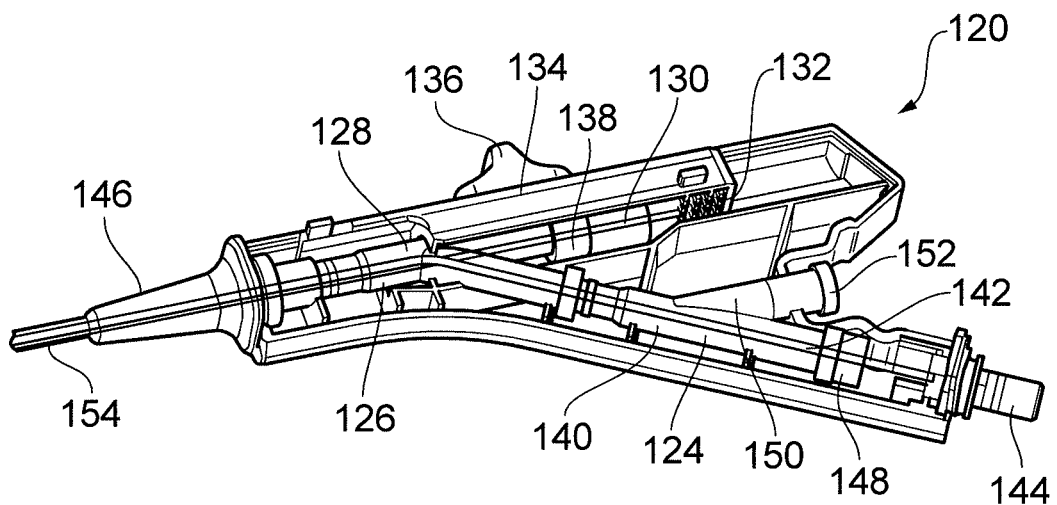
FIG. 3 is a cut away perspective view of the interface joint shown in FIG. 2.

FIGS. 2 and 3 show the structure of an interface joint 120 that is an embodiment of the invention. The interface joint comprises a hard plastic shell 122, which encases several internal components. In FIGS. 2 and 3 one half of the shell 122 is removed to show the inside of the joint. The shell 122 is in the shape of a pistol, i.e. it has an upper barrel portion 121 and a lower adjoining portion 123 which extends away from a proximal end of the upper barrel portion at an oblique angle. The upper barrel portion 121 contains the needle movement mechanism, while the lower adjoining portion 123 contains the connections for the fluid and energy feeds.

The core of the interface joint 120 is a pair of Y-shaped conduits 124, 126 which are mated together to define a branched passageway. The Y-shaped conduits may be made from polycarbonate or other suitable hard plastic, and are shown in more detail in FIGS. 16A and 16B. A first length 128 of the branched passageway is mounted in and lies along the upper barrel portion 121 of the shell 122. The first length 128 receives at its proximal end a push rod 130 for controlling deployment of the retractable needle. The push rod 130 has a crooked proximal end 132, which is mounted, e.g. heat staked, in a needle slider 134. The needle slider 134 is slidably mounted in the upper barrel portion 131. The needle slider 134 includes a protruding thumb trigger 136 for moving the slider to and fro, which causes the needle to slide in and out of the distal assembly. The proximal end of the first length 128 is sealed by a silicone bung 138, which is shown in more detail in FIGS. 15A and 15B.

A second length 140 of the branched passageway is mounted in and lies along the lower adjoining portion 123, i.e. at an oblique angle to the first length 128. The second length 140 conveys a coaxial cable 142 from a proximal QMA-type connector 144 to the proximal end of the first length 128, where it meets the push rod 130 and exits the interface joint 120 through the distal outlet 146. The QMA-type connector 144 is connected to the interface cable from the generator. The coaxial cable 142 may be a Sucoform 047 coaxial cable coated in a 30.mu.m layer of Parylene C. The coaxial cable 142 may pass through a silicone sealing plug 148 at the proximal end of the second length 140.

A third length 150 of the branched passageway leads off from the second length 140 to provide a outward facing fluid receiving port 152. The fluid receiving port 152 may be a threaded luer lock fitting, for sealing engagement with a suitable syringe or the like. The sealing plug 148 and the bung 138 cause the branched passageway to be sealed in a watertight manner, whereby fluid introduced at the fluid receiving port 152 can only exit the interface joint 120 through the distal outlet 146.

The distal outlet 146 of the interface joint receives therethrough a proximal portion of the flexible shaft 154 that is introduced into the instrument channel of the endoscope. The flexible shaft conveys the fluid, push rod 130 and coaxial cable 142 as discussed below. A proximal end of the flexible shaft 154 is directly bonded into the branched passageway so that there is some overlap along the upper barrel portion 121. This bonded junction is masked by a covering 156 (e.g. of silicone rubber) which fits like a stretched glove and is bonded in place. The covering 156 operates as a strain relief element, and also doubles as an end of shaft flexible bend restrictor.

The primary user of the interface joint 120 may be the endoscopist's assistant. In use, the operator typically offers the distal tip of the instrument to the endoscopist for insertion down the working channel of the flexible endoscope, makes the electrical connection between interface joint 120 and the interface cable (which is connected to the generator) and then supports the interface joint 120 itself throughout the procedure. During the procedure the operator can inject the distension/marker fluids as required via 5 to 20 ml syringes attached to the fluid receiving port 152 and operate the needle slider 134 as instructed by the endoscopist.

The flexible shaft 154 comprises an outer cannula tube that contains the coaxial cable 142, push rod 130 and fluid. The specific internal structure of the flexible shaft is discussed below with reference to FIG. 10. The distal assembly is fixed to the outer cannula tube in a manner that means any rotation applied to the tube is passed to the distal assembly. Accordingly, to permit rotatable manipulation of the distal assembly, a torque transfer unit is mounted on the flexible shaft in order to facilitate rotation thereof.

Figure 4A:
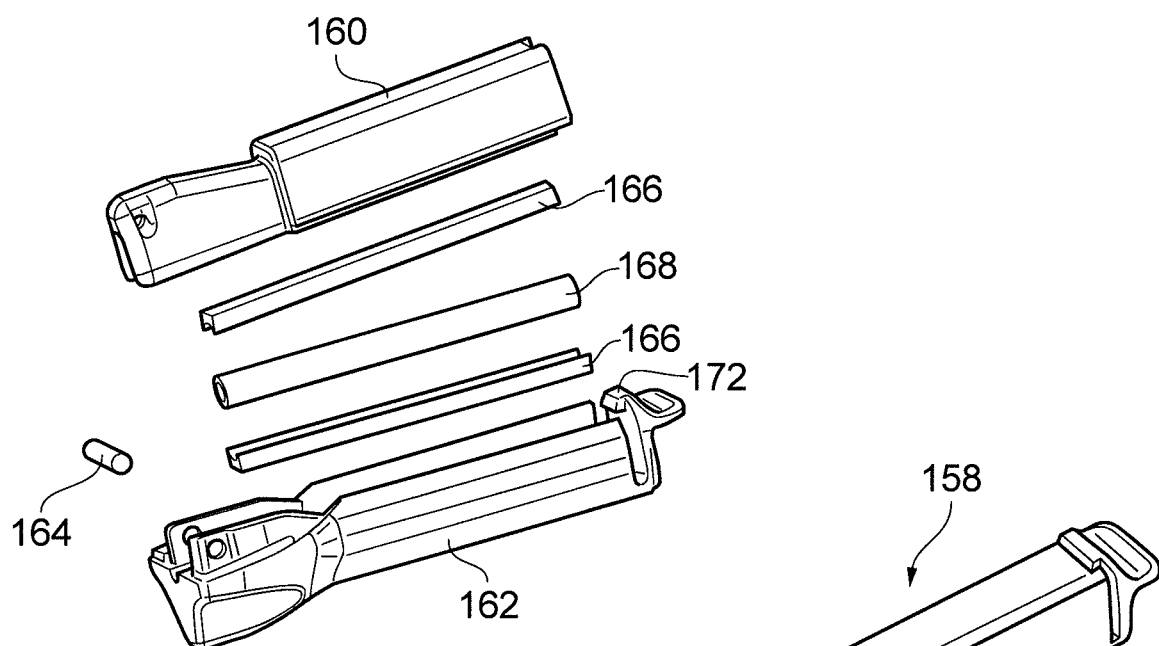
FIG. 4A is an exploded view of a torque transfer unit that is an embodiment of the invention.
Figure 4B:
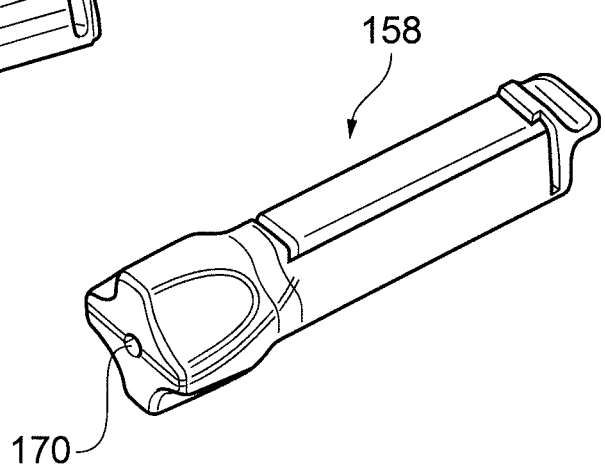
FIG. 4B is a perspective view of the torque transfer unit of FIG. 4A in an assembled state.

FIGS. 4A and 4B show a torque transfer unit 158 that is an embodiment of the invention. Essentially the torque transfer unit 158 is an elongate clamp that imparts a gripping force along a length of the flexible shaft. By gripping a length of the shaft, the torque transfer unit can apply a lower maximum pressure, and therefore prevent damage to the flexible shaft and its contents.

As shown in FIG. 4A, the torque transfer unit 158 comprises an upper elongate housing member 160 and a lower elongate housing member 162, which are hinged together about a pivot rod 164 at a distal end thereof. The upper elongate housing member 160 and the lower elongate housing member 162 each carry a U-shaped clamping member therein 166. The clamping members 166 oppose one another, whereby pivoting the upper elongate housing member 160 and the lower elongate housing member 162 relative to each other alters the distance between the clamping members 166. A deformable tube 168 is mounted between the clamping members 166. The deformable tube 168 is threaded on to the flexible shaft, which passes though holes 170 in the distal and proximal faces of the torque transfer unit 158. In use, the upper elongate housing member 160 and the lower elongate housing member 162 are pivotable between a release position in which the torque transfer unit can be slid up and down the flexible shaft, and a clamping position, in which the deformable tube 168 is squashed between the clamping members to impart a gripping force on the flexible shaft. The upper elongate housing member 160 and the lower elongate housing member 162 can be retained in the clamping position by a releasable clip 172. The distal end of the torque transfer unit 158 has a series of circumferential indentations designed to be gripped by the thumb and forefinger of the operator, to facilitate rotation.

Figure 5:
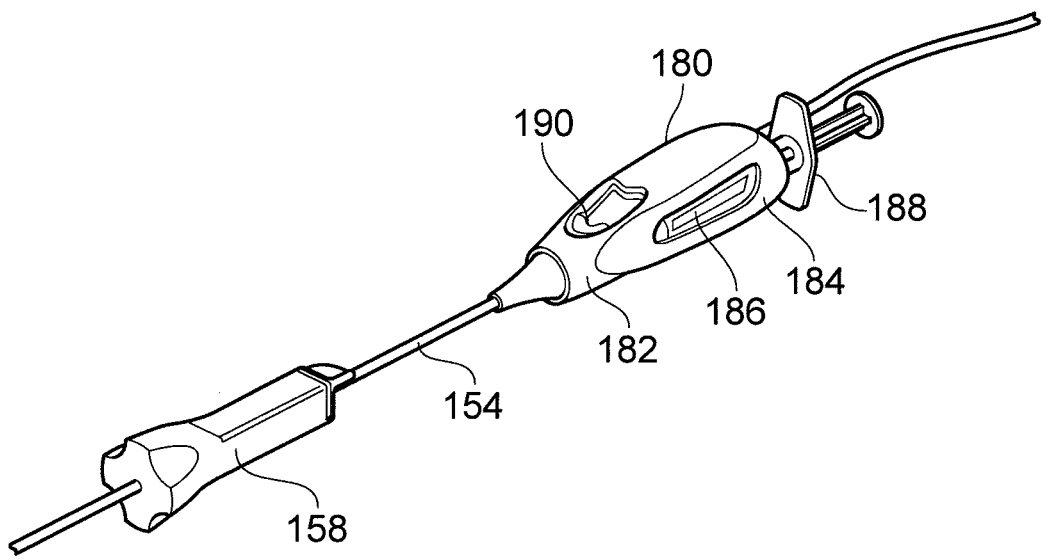
FIG. 5 is a schematic perspective view of another interface joint that is an embodiment of the invention.

FIG. 5 is a perspective view of an interface joint 180 in conjunction with a torque transfer unit 158 that is another embodiment of the invention. The torque transfer unit 158 is the same as that discussed above with reference to FIGS. 4A and 4B and is not discussed again.

The interface joint 180 in this embodiment comprises a compact barrel-like body 182, which facilitates rotation by the endoscopist's assistant. In particular, the interface cable 104 is connected in axial alignment with the body 182, e.g. via a snap-fit rotary coaxial connector. The body 182 includes a nested barrel 184 for receiving a syringe 188 to deliver fluid. The nested barrel 184 may include a viewing window 186 to show how much fluid remains.

In this embodiment, a needle slider control 190 is mounted towards the nose of the body 180 for thumb control whilst the body 182 is supported in the palm of the hand. The slider 190 may have free reciprocal movement as in the embodiment shown in FIGS. 2 and 3. A latch mechanism (not shown) may be provided to lock and park the slider in the fully retracted needle position. Alternatively the slider may have a spring-loaded action which biases the mechanism into the retracted state. With the sprung loaded option the user (assistant) would need to hold the slider forward against the spring whilst injecting the fluid.

Figure 6:
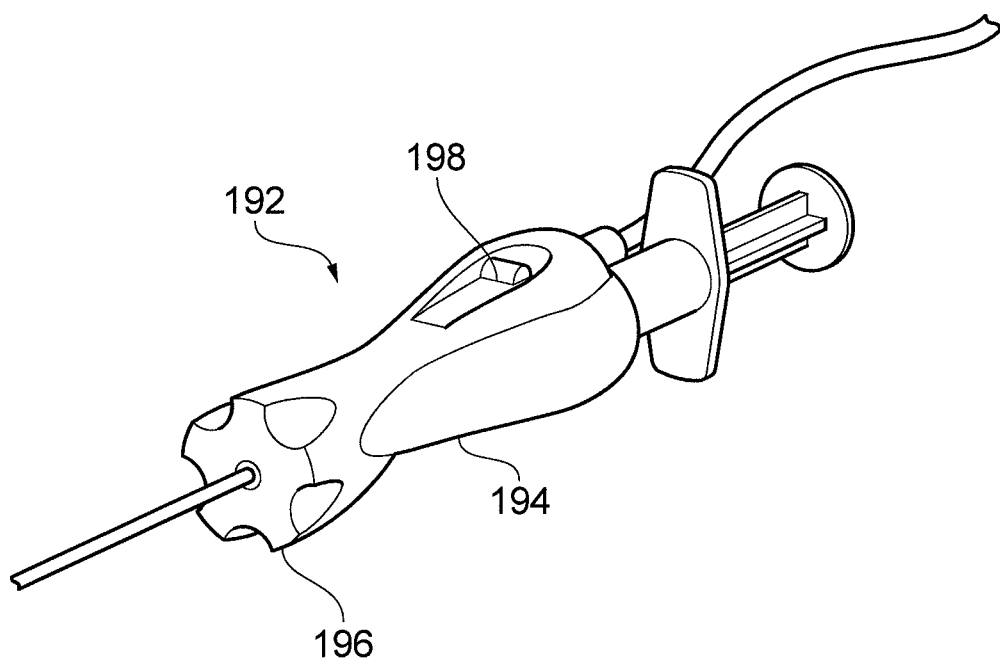
FIG. 6 is a schematic perspective view of an integrated interface joint and torque transfer unit that is an embodiment of the invention.

FIG. 6 is a perspective view of a combined interface joint and torque transfer unit 192 that is another embodiment of the invention. All functions of the separate torque transfer unit and interface joints discussed above are provided here within a single moulded assembly. However, the combined unit is not able to slide along the flexible shaft in use, which means that the instrument length should be closely matched to the endoscope working channel length. However, an advantage of this arrangement is that there is more microwave power available at the active tip in the distal assembly because a shorter instrument length means less power is lost.

The combined unit 192 comprises a waisted barrel 194 with a faceted distal end 196 to facilitate easy finger and thumb rotary control. A needle slider 198 is mounted towards the back of the barrel 194 due to the natural hold and support position by the endoscopist during these procedures.

As an alternative to the needle slider 198, a hinged rocker type control lever could be used for ease of thumb control. With this design needle slider (or rocker) latch forward and back would be required or latch back and sprung forward control to enable one handed operation and fluid injection by the endoscopist, i.e. to give the endoscopist the freedom to use their second hand to hold or manipulate the endoscope.

Figure 7:
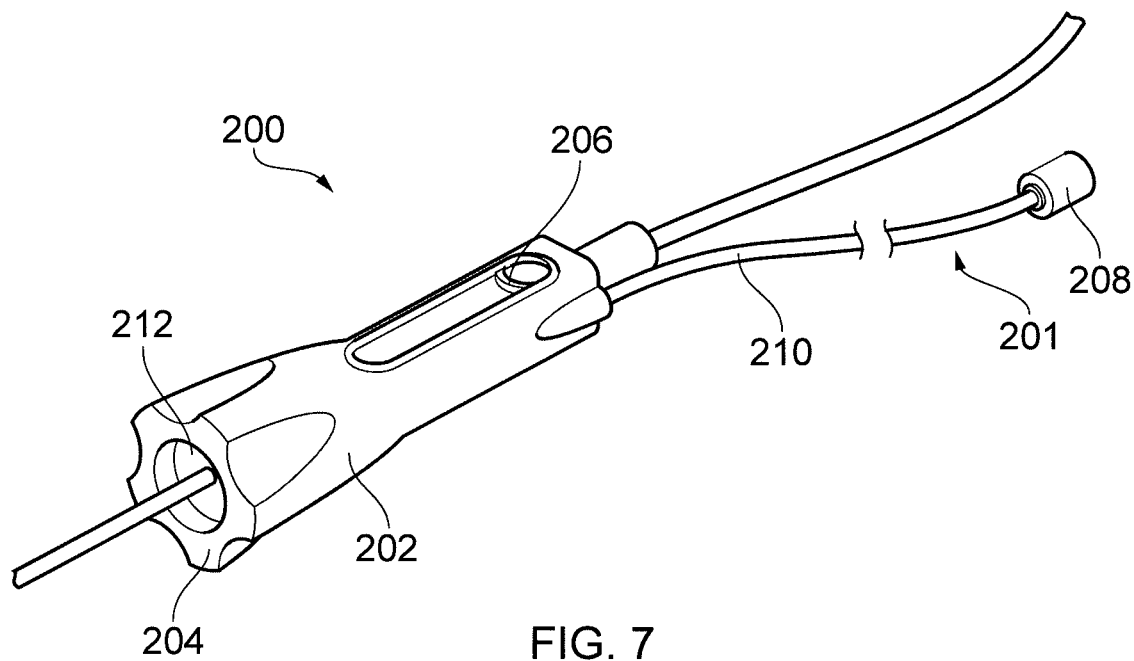
FIG. 7 is a schematic perspective view of another integrated interface joint and torque transfer unit that is an embodiment of the invention.

FIG. 7 is a perspective view of a combined interface joint and torque transfer unit 200 that is another embodiment of the invention. The combined unit 200 is similar to the device shown in FIG. 6 except for a remote syringe fluid injection coupling 201. The combined unit 200 comprises a slim barrel-like body 202 with a faceted distal end 204 and a needle slider 206 which function as discussed above. The body 202 has a slim, compact design because it does not also need to house a syringe. Instead, the body 202 is connected to a fluid receiving port 208 via a fluid feed line 210. This arrangement may permit the device to be used with larger syringes of unrestricted barrel diameter. The body in this arrangement may also be more lightweight than that shown in FIG. 6. In this embodiment the distal end 204 of the body 202 includes a recessed flat face 212, which allows abutted location against the endoscope port cap for added stability. As with this device shown in FIG. 6, this solution (as shown) requires the instrument length to be closely matched to the third party endoscope working channel length, and thereby offers the potential for more microwave power availability at the instrument tip.

It may be possible to build in short axial adjustment of up to 100 mm within the combined barrel-shaped units shown in FIGS. 6 and 7. This may enable the endoscopist to fine tune the instrument length to his/her flexible endoscope of choice. This added functionality could also minimise the number of product variants required to cover the range of present day third party endoscopes.

FIGS. 15A, 15B, 16A and 16B show further details of some of the internal components of the interface joint.

FIGS. 15A and 15B are respectively perspective and cross-sectional views of the bung 138 that seals the proximal end of the first length of the branched passageway. The bung comprises a rotary luer lock fitting 246 and a integral sealing diaphragm 248, e.g. made of resiliently deformable rubber.

FIGS. 16A and 16B show the Y-shaped conduits 250 from which the branched passageway is formed. Each Y-shaped conduit has a main linear channel between a first inlet 252 and an outlet 254, and a second channel at an oblique angle to the main linear channel, the second channel having a second inlet 256 and joining the main linear channel about halfway along its length. Each of the first inlet 252 and the second inlet 256 has a rotary luer lock fitting 258.

Distal Assembly Configuration

Figure 8:
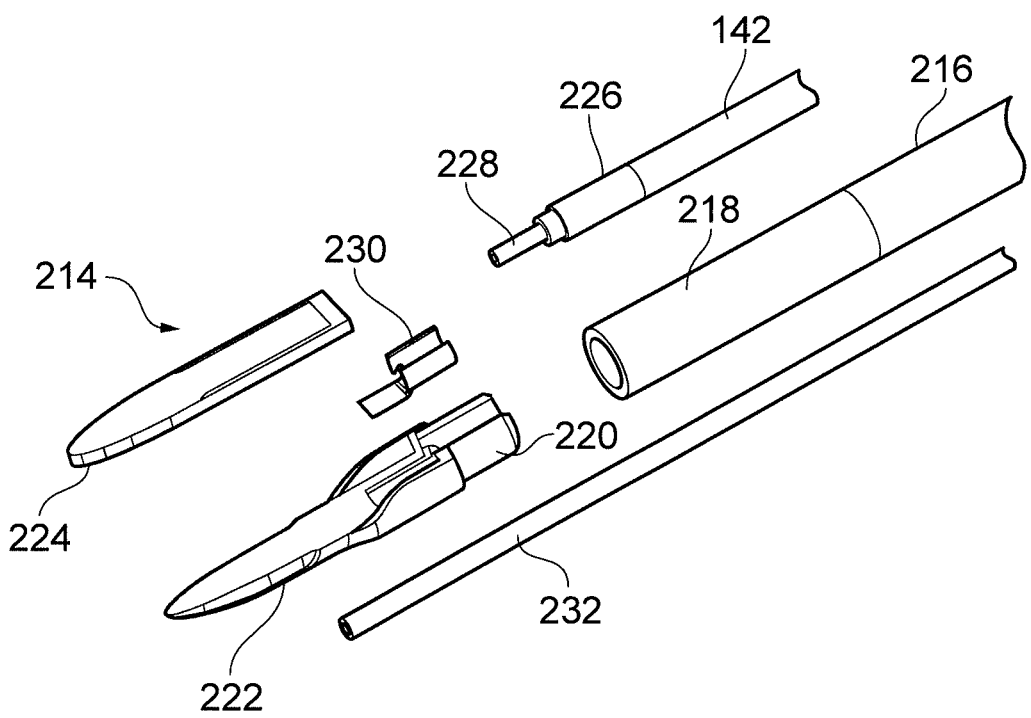
FIG. 8 is an exploded view of a distal end assembly for an electrosurgery device that is an embodiment of the invention.
Figure 9A:
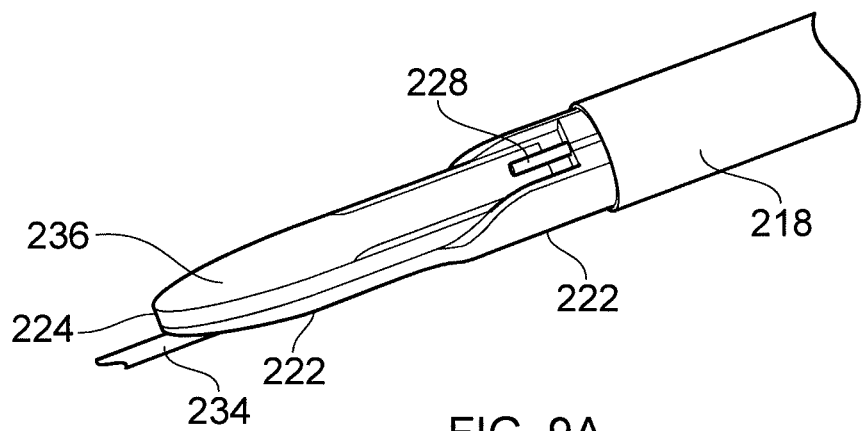
FIG. 9A is a top perspective view of the distal end assembly of FIG. 8 in an assembled state.
Figure 9B:
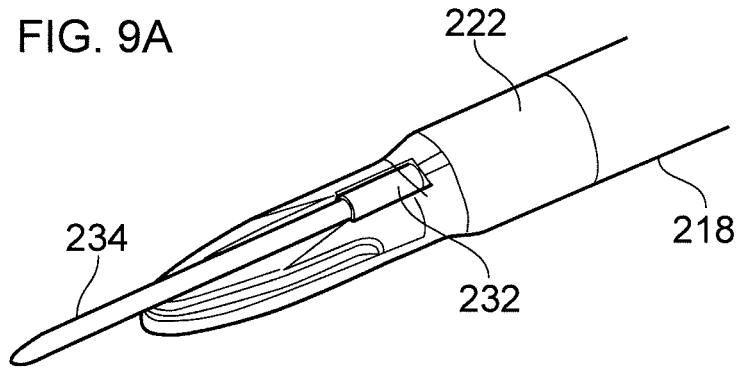
FIG. 9B is a bottom perspective view of the distal end assembly of FIG. 8 in an assembled state.

FIGS. 8, 9A and 9B show details of a distal assembly 214 comprising an active tip that is an embodiment of the invention. FIG. 8 shows an exploded view of the components that form the distal assembly 214. The distal assembly 214 is mounted at the distal end of the outer cannula tube 216 of the flexible shaft 154 that is discussed above. In order to provide a torque transfer function, the majority of the outer cannula tube 216 is formed of a braided tube, e.g. comprising a braided wire (e.g. stainless steel) wrap mounted between a radially inner polymer layer and a radially outer polymer layer. However, to avoid the braid material from interfering with the deliver of RF and/or microwave frequency EM energy to the distal assembly, a distal portion 218 of the outer cannula tube 216 is made purely of the polymer layers, i.e. without an internal braid.

The distal portion 218 of the outer cannula layer 216 fits on to a corresponding proximal part 220 of a protective hull 222. The protective hull is formed from polyether ether ketone (PEEK) or any other suitable engineering plastic, and is shaped to perform a number of functions, i.e.
  mount the distal assembly on the flexible shaft,
  provide a protective undersurface for the active tip,
  provide a protective housing for the needle, and
  locate the active tip relative to the coaxial cable.
The parts of the structure of the hull 222 that perform these functions are discussed in more detail below with reference to FIGS. 14A and 14B.

The distal assembly 214 includes an active tip 224, which is a planar piece of dielectric material (e.g. alumina) having conductive layers (e.g. of gold) on its upper and lower surfaces. The distal end of the active tip 224 is curved. The conductive layers are electrically connected to the inner and outer conductors of the coaxial cable 142 that is conveyed by the flexible shaft 216. At the distal end of the coaxial cable 142, its outer sheath is removed to expose a length of the outer conductor 226. The inner conductor 228 of the coaxial cable extends beyond the distal end of the outer conductor 226. The coaxial cable 142 and the active tip 224 are mounted relative to one another so that the protruding part of the inner conductor 228 lies on a first conductive layer of the active tip, while the outer conductor 226 is brought into electrical connection with a second conductive layer by a conductive adaptor element 230. The first conductive layer is isolated from the outer conductor 226 and the second conductive layer is isolated from the inner conductor 228. Further details of the configuration of the active tip are discussed below with reference to FIGS. 11A to 11C.

When assembled, as shown in FIGS. 9A and 9B, the active tip 224 and coaxial cable 142 are bonded to each other and to the hull 222 by the application of epoxy adhesive over the portion of the inner conductor 228 that projects from the outer conductor. This epoxy adhesive also serves to form an end plug for the outer cannula tube, i.e. a fluid tight seal that means the only exit for fluid introduced at the interface joint is through the needle.

The hull 222 includes a recess for retaining a needle guide tube 232, e.g. made of polyimide. In use the distal assembly 214 makes an intimate contact with the patient. The needle 234 can be extended beyond the distal end of the active tip 224 and retracted to a position back inside the guide tube 232 via control of the slider mechanism on the interface joint. In its extended position, the needle is used by the endoscopist to inject fluid for the purpose of locally distending and marking tissue. The conductive layers on the active tip 224 form bi-polar electrodes for delivering RF and/or microwave frequency energy.

The needle guide 232 extends back inside and proximal to the distal assembly to provide extended creepage clearance to ensure RF/microwave activation only occurs across the distal tip region of the active tip 224.

Similarly it can be seen that the conductive layer 236 is recessed back in behind the distal tip region of the active tip 224. This is done on both upper and lower faces to increase the tracking/creepage distance at the proximal end of the active tip, further ensuring that RF/microwave energy is focused towards the distal end and intentional active element of the tip.

Figure 10:
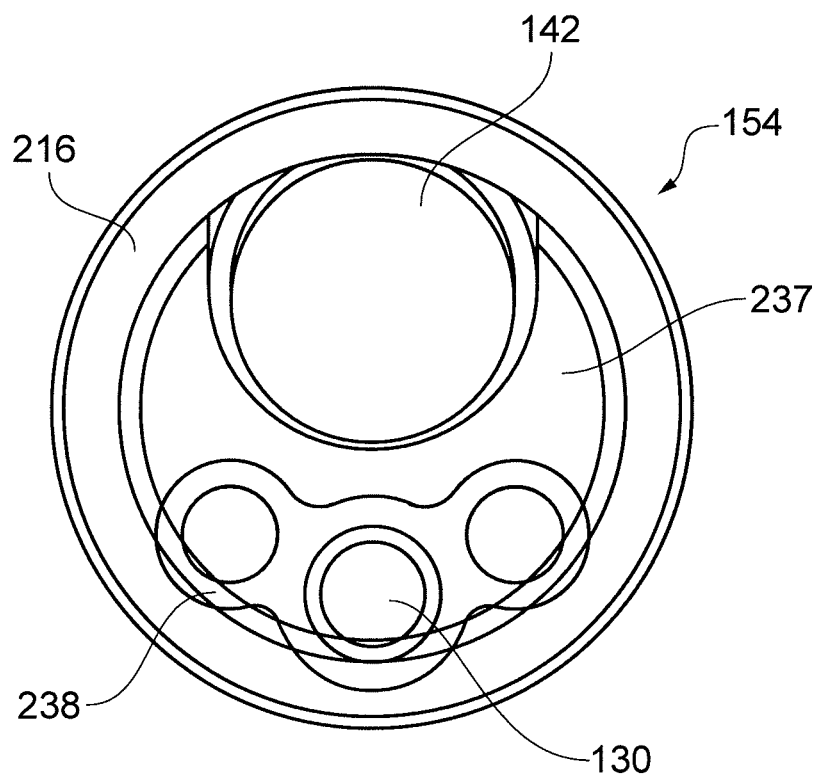
FIG. 10 is a cross-sectional view of an interface cable suitable for use with the present invention.

FIG. 10 shows a typical cross section of the flexible shaft 154. The flexible shaft may run for 2.3 m (or 2.0 m), i.e. the entire length of the instrument connecting the interface joint to the distal assembly. During use the majority of this shaft length sits within the working channel of the flexible endoscope. The flexible shaft 154 comprises the outer cannula tube 216 (i.e. the braided tube discussed above), which forms a fluid tight cannula 237 and electrical barrier between user/patient, and the coaxial Sucoform cable 142 which in itself is further insulated. The outer cannula tube 216 also houses a 3-lumen PTFE extruded tube 238 which provides a low friction pathway for the push rod 130 and stability/support to the construction whilst ensuring a fluid pathway is maintained along the full length of the cannula at all times.

Through the length of the flexible shaft 154, the coaxial cable 142 (e.g. Sucoform 047 cable) forms one lumen of a composite construction with the braided and double insulated outer cannula tube 216 forming the flexible protective instrument shaft. To manage the potential thermal risk posed in use activation controls may be imposed on the use of microwave energy by the generator. For example, in the first application instance activation may be limited to 20 s (continuous output), and thereafter the average power incidence on the proximal end of the distal assembly may be limited to 4 W. This control may be imposed independently of the endoscopist, e.g. via the generator software. With this control in place a temperature of 40° C. has been observed after 20 s continuous activation on the polymer surface of the instrument shaft immediately distal of the interface joint. After 20 s the temperature then falls as further continuous microwave activation by the Endoscopist is automatically interrupted by the generator software. Full 20 s activation capacity may be prevented until 240 s (12×20 s) has elapsed.

In practice, it may not be necessary to activate the coagulation function for longer than 10 s due to concerns over perfusion at the tip resulting in potential full wall thickness injury to the bowel wall.

Figure 11A:
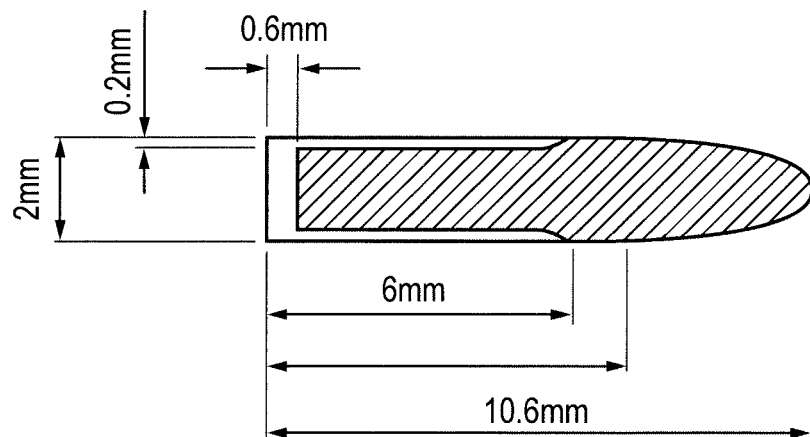
FIG. 11A is a top view of a bipolar structure used in the distal end assembly of FIG. 8.
Figure 11B:
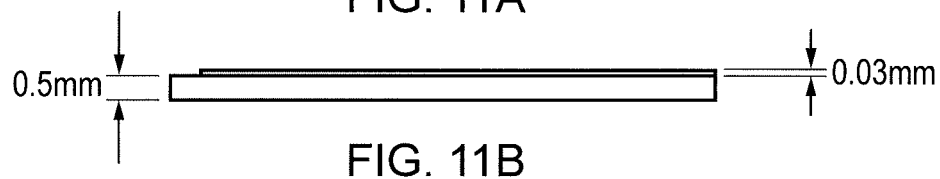
FIG. 11B is a side view of a bipolar structure used in the distal end assembly of FIG. 8.
Figure 11C:
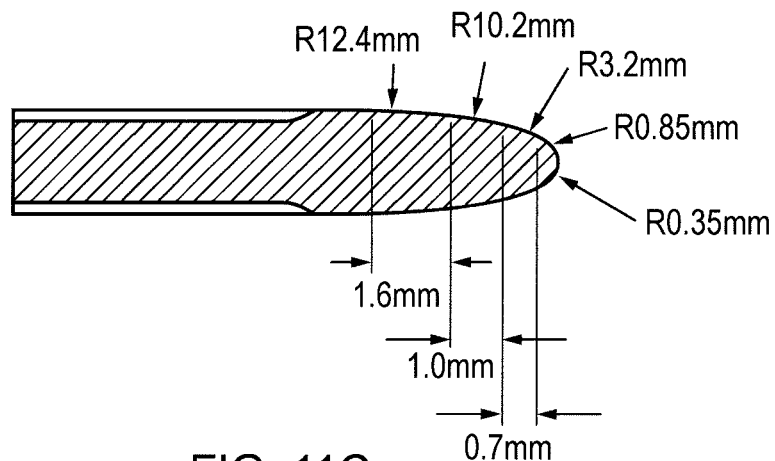
FIG. 11C is a bottom view of a bipolar structure used in the distal end assembly of FIG. 8.

FIGS. 11A, 11B and 11C illustrate the dimensions of one example of an active tip 224 that can be used in embodiments of the invention. The overall length of the active tip is 10.6 mm, with a maximum width of 2 mm and a height of 0.5 mm. The layer of metallisation on the active tip has a thickness of 0.03 mm. The curved distal end is manufactured as a plurality of radiused sections of decreasing length and radius towards the distal tip. In this embodiment there are five different radiused section, but more could be used. The length of each section and its corresponding radius of curvature is given in Table 1:

TABLE 1

| Curvature at distal end of active tip | |
|---|---|
| Section length (mm) | Radius of Curvature (mm) |
| 1.6 | 12.4 |
| 1.0 | 10.2 |
| 0.7 | 3.2 |
| 0.2 | 0.85 |
| 0.1 | 0.35 |

As mentioned above, the conductive layers on both surface are set back from the edges of the dielectric substrate by a distance of 0.2 mm along the proximal 6 mm of the tip. And to ensure that the top conductive layer is isolated from the outer conductor of the coaxial cable, the top conductive layer is set back from the proximal edge of the dielectric substrate by a distance of 0.6 mm.

Figure 12A:
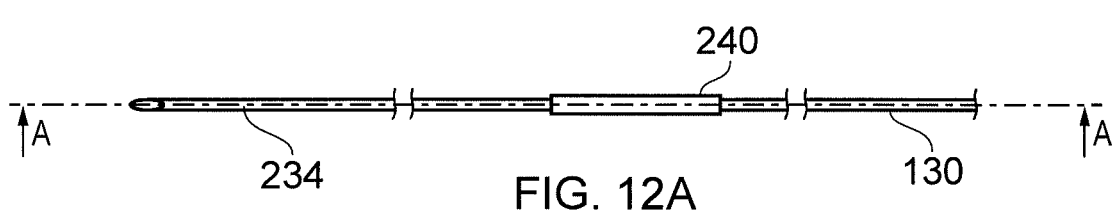
FIG. 12A is view of a needle assembly suitable for use with the distal end assembly of FIG. 8.
Figure 12B:
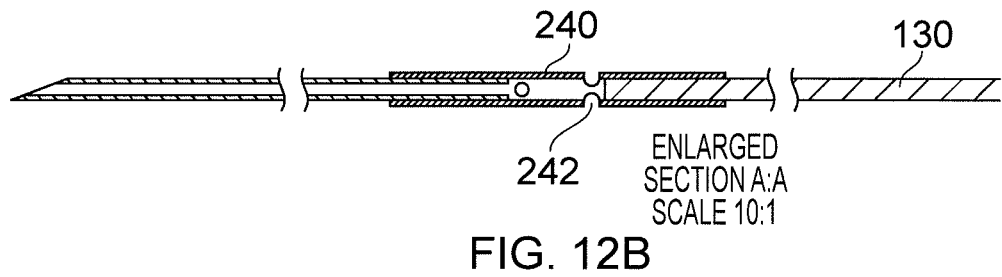
FIG. 12B is an enlarged cross-sectional view through the needle assembly shown in FIG. 12A.

FIGS. 12A and 12B depict the transition from the push rod 130 to the needle 234. A needle ferrule 240 is connected to the push rod 130 at a proximal end thereof and is connected to the needle 234 at a distal end thereof. A set of holes in the outer surface of the needle ferrule 240 permits ingress of fluid from the flexible shaft for delivery out of the needle 234. As shown in FIG. 12B, the push rod 130 acts as a stopper in the proximal end of the ferrule 240, thereby preventing fluid from escaping in the wrong direction.

Figure 13:
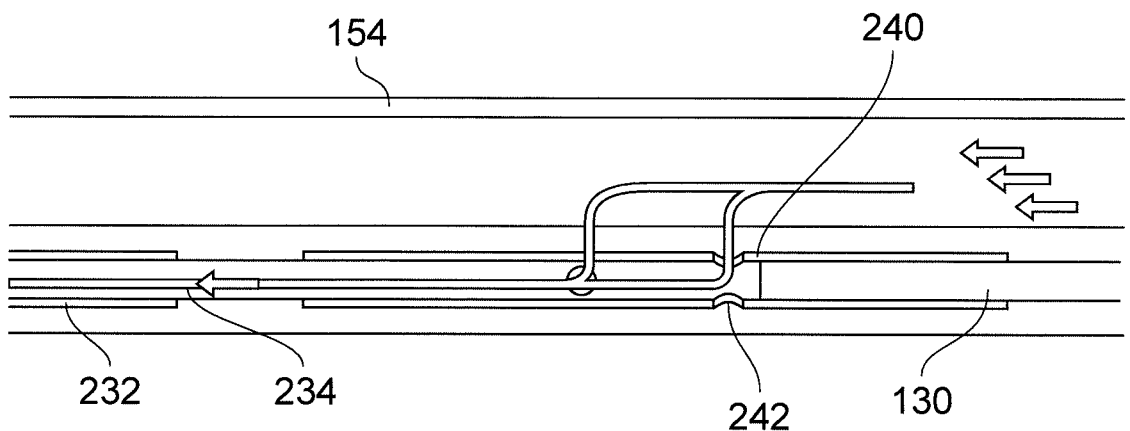
FIG. 13 is a schematic drawing illustrating a fluid flow path through an interface cable that is suitable for use with the present invention.

FIG. 13 illustrates schematically the flow path for the fluid. Immediately proximal of the distal assembly the injected fluid that has passed down the flexible shaft 154 from the syringe is forced through four small radial holes 242 central to the needle ferrule 240 and thence into the hypodermic needle 234 for injection into the patient.

Figure 14A:
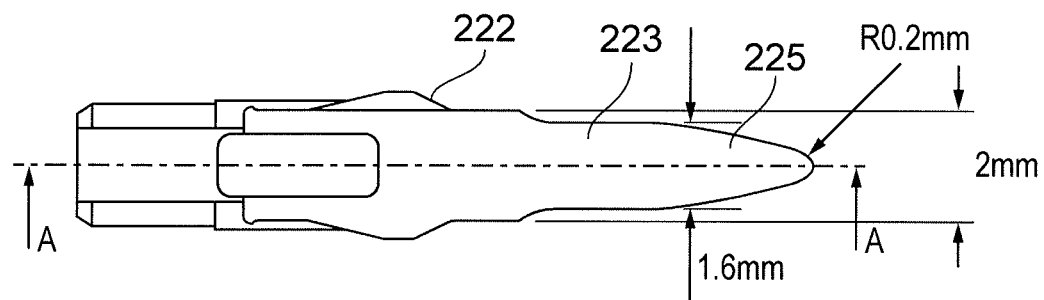
FIG. 14A is a top view of a protective hull used in the distal end assembly of FIG. 8.
Figure 14B:
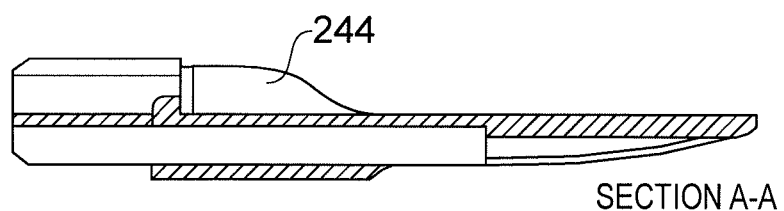
FIG. 14B is a cross-sectional view through the protective hull used in the distal end assembly of FIG. 8.

FIGS. 14A and 14B show the shape of the protective hull 222. As shown more clearly in FIG. 9B, the distal end of the hull is shaped to permit the active tip to overhang it by around 0.2 mm around the distal edge except at the distal tip. The surface that contacts the underside of the active tip therefore has a maximum width of 2 mm, which narrows to 1.6 mm in an intermediate portion 223 before tapering to its distal tip in a distal portion 225. The distal tip may be a single radiused curve, e.g. having a radius of 0.2 mm.

Meanwhile the proximal end of the hull defines an oblong recess for receiving the proximal end of the active tip. The oblong recess is bordered by a pair of wings 244 on each side, which act to retain and align the active tip as well as define a volume for receiving the adhesive that covers the exposed inner conductor of the coaxial cable.

Figures 17A, 17B:
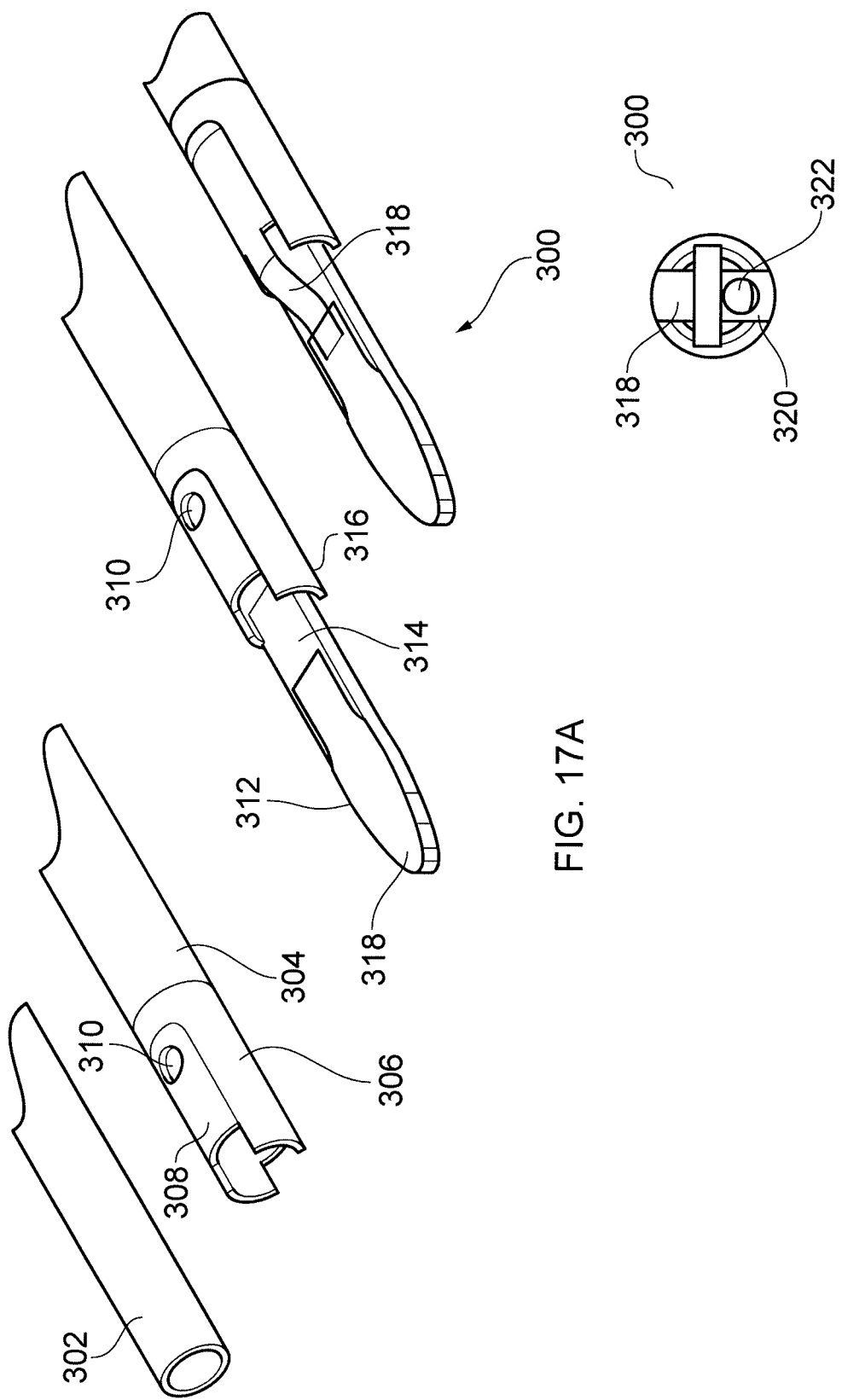
FIG. 17A is an isometric view of various stages in the fabrication of a distal end assembly for an electrosurgery device that is an embodiment of the invention.
FIG. 17B is an end view of the complete distal end assembly shown in FIG. 17A.

FIG. 17A shows various stages in the assembly of a distal end portion 300 for an electrosurgical instrument that is another embodiment of the invention. The leftmost view in FIG. 17A shows an inner tube 302 made of a conductive material. This inner tube 302 represents the inner conductor of the coaxial feed discussed above. The second view from left in FIG. 17A shows an outer tube 304, which first over the inner tube 302. The outer tube 304 may be formed as a tube of insulating dielectric material having a conductive coating on its outer surface. The conductive coating acts as the outer conductor of the coaxial feed.

At the distal end of the outer tube, a portion of the conductive coating is etched away to expose a portion 306 of dielectric material. An island 308 of conductive coating is left on the top surface of the outer tube at its distal end. The island 308 is separated (i.e. electrically isolated) from the rest of the conductive coating 304 by the exposed portion 306 of dielectric material. A tongue (not shown) of conductive coating is formed on the bottom surface of the outer tube at its distal end with a similar shape and size to the island 308. However, the tongue remains in electrical contact with the rest of the conductive coating, i.e. it is an extension of the outer conductor.

A hole 310 (e.g. having a diameter of 1 mm) is formed in the island 308 through the conductive coating and insulating dielectric material, thereby exposing the inner tube 302. The hole is then filled with a conductive material (e.g. epoxy silver) in order to electrically connect the inner tube 302 with the island 308. As a result, the distal end of the outer tube has two opposed electrical contacts on its outer surface. A first contact (the island 308) is in electrical connection with the inner tube 302 (i.e. inner conductor) and a second contact (the tongue) is in electrical connection with the conductive coating of the outer tube 304 (i.e. outer conductor).

The third view from left in FIG. 17A shows the next stage in assembly, where an instrument tip 312 is inserted into the distal end of the outer tube 304. The instrument tip 312 comprises a planar piece 314 of rigid dielectric, e.g. ceramic, such as alumina. The outer tube 304 has two opposing tabs 316, which can receive and retain the planar piece 314, e.g. as an interference fit or using suitable adhesive.

The side edges of the planar piece 314 taper in a quasi-parabolic manner towards the distal end thereof. The flat upper and lower surfaces have conductive layers, e.g. of gold or silver metallisation, formed thereon. The upper layer 318 is visible in FIG. 17A.

The right most view in FIG. 17A shows the final stage of assembly, in which the first and second contacts are electrically connected respectively to the upper and lower conductive layers on the instrument tip 312 using a piece of conductive foil 318.

FIG. 17B shows an end view of the distal end portion 300 after assembly. Here it can be seen that the lower piece of conductive foil 320 has a hole 322 formed therein through which the retractable needle discussed above can pass.

The invention claimed is:

1. An interface joint for interconnecting an electrosurgical generator and an electrosurgical instrument, the interface joint comprising:
   a housing made of electrically insulating material, the housing having:
      a first inlet for receiving radiofrequency (RF) electromagnetic (EM) energy or microwave frequency EM energy from the electrosurgical generator,
      a second inlet for receiving fluid, and
      an outlet;
   a single cable assembly for connecting the outlet to the electrosurgical instrument, the single cable assembly comprising a flexible sleeve which defines a fluid flow path that is in fluid communication with the second inlet, and which conveys a coaxial cable that is connected to the first inlet; and
   a slidable trigger on a surface of the housing, the slidable trigger being attached to a push rod that extends out of the housing through the outlet.

2. An interface joint according to claim 1, wherein the housing includes an internal watertight branched passageway which defines a fluid flow path between the second inlet and the outlet, and wherein the internal watertight branched passageway has a first port adjacent to the first inlet for admitting the coaxial cable.

3. An interface joint according to claim 2, wherein the first port comprises a sealing bung which defines a watertight passage for the coaxial cable.

4. An interface joint according to claim 2, wherein the internal watertight branched passageway is formed from a pair of Y-shaped conduits.

5. An interface joint according to claim 1, wherein the housing includes an internal watertight branched passageway which defines a fluid flow path between the second inlet and the outlet, and wherein the internal watertight branched passageway has a first port adjacent to the first inlet for admitting the coaxial cable and a second port adjacent the slidable trigger for admitting the push rod.

6. An interface joint according to claim 5, wherein the second port comprises a sealing bung which defines a watertight passage for the push rod.

7. An interface joint according to claim 5, wherein a distal end of the push rod is connected to a proximal end of a needle ferrule, which has an internal volume in fluid communication with the fluid flow path through the flexible sleeve, and wherein a needle is mounted in a distal end of the needle ferrule in fluid communication with the internal volume.

8. An interface joint according to claim 1, wherein the cable assembly has an outer diameter in the range 1.2 mm to 9 mm.

9. An interface joint according to claim 1, wherein the flexible sleeve has spiral wound reinforcement or spiral wound multiple cross braiding therein to assist in the transfer of torque.

10. An interface joint according to claim 9, wherein the spiral wound reinforcement or spiral wound multiple cross braiding has a variable pitch.

11. An interface joint according to claim 1, wherein the housing comprises a strain relief element mounted in the outlet and surrounding the flexible sleeve.

12. An interface joint according to claim 1 having a second coaxial cable attached to the first inlet via an interface connection, wherein the interface connection is arranged to permit relative rotation of the interface joint relative to the second coaxial cable.

13. An interface joint according to claim 1, wherein the flexible sleeve comprises a multi lumen tube.

14. An interface joint according to claim 13, wherein the flexible sleeve includes an extruded separator element inserted inside a single lumen tube, the extruded separator element including a plurality of through channels.

15. An interface joint according to claim 1, wherein the housing is an elongate capsule sized to fit in an operator's hand.

\* \* \* \* \*